(12) United States Patent
Yamada et al.

(10) Patent No.: US 8,334,122 B2
(45) Date of Patent: Dec. 18, 2012

(54) THERMOTOLERANT ETHANOL-PRODUCING YEAST AND ETHANOL PRODUCTION METHOD UTILIZING THE SAME

(75) Inventors: Mamoru Yamada, Yamaguchi (JP); Limtong Savitree, Bangkok (TH)

(73) Assignee: Yamaguchi University, Yamaguchi (JP)

( * ) Notice: Subject to any disclaimer, the term of this patent is extended or adjusted under 35 U.S.C. 154(b) by 282 days.

(21) Appl. No.: 12/514,420

(22) PCT Filed: Nov. 20, 2007

(86) PCT No.: PCT/JP2007/001270
§ 371 (c)(1),
(2), (4) Date: Jun. 16, 2009

(87) PCT Pub. No.: WO2008/062558
PCT Pub. Date: May 29, 2008

(65) Prior Publication Data
US 2010/0062506 A1    Mar. 11, 2010

(30) Foreign Application Priority Data
Nov. 20, 2006  (JP) ................................ 2006-313162
Mar. 22, 2007  (JP) ................................ 2007-075137

(51) Int. Cl.
*C12P 7/06*    (2006.01)
*C12N 9/00*    (2006.01)
*C12N 1/00*    (2006.01)
*C12N 15/00*   (2006.01)
*C07H 21/02*   (2006.01)

(52) U.S. Cl. ..................... 435/161; 435/183; 435/254.2; 435/255.1; 435/320.1; 536/23.2

(58) Field of Classification Search ........................ None
See application file for complete search history.

(56) References Cited

FOREIGN PATENT DOCUMENTS

| JP | 60-034188 | 2/1985 |
| JP | 63-042690 | 2/1988 |
| JP | 05-336951 | 12/1993 |
| JP | 06-303968 | 11/1994 |
| JP | 2000-050894 | 2/2000 |
| JP | 2001-069979 | 3/2001 |
| JP | 2003-520045 | 7/2003 |
| JP | 2006-514831 | 5/2006 |
| JP | 2006-280253 | 10/2006 |

OTHER PUBLICATIONS

Banat et al., "Characterization and Potential Industrial Applications of Five Novel, Thermotolerant, Fermentative, Yeast Strains," World Journal of Microbiology and Biotechnology, vol. 11, pp. 304-306, 1995.
Banat et al., "Isolation of Thermotolerant, Fermentative Yeasts Growing at 52 degree and Producing Ethanol at 45 Degree and 50 degree," World Journal of Microbiology and Biotechnology, vol. 8, pp. 259-263, 1992.
Institute for Fermentation, Osaka (IFO) List of Cultures 2000 Microorganisms, Eleventh Edition, Jan. 31, 2001, pp. 57-59.
Limtong, et al., "Production of Fuel Ethanol at High Temperature from Sugar Cane Juice by a Newly Isolated Kluyveromyces Marxianus," Bioresource Technology, 2007, vol. 98, No. 17, May 2007, pp. 3367-3374.
Lertwattanasakul, et al., "Comparison of the Gene Expression Patterns of Alcohol Dehydrogenase Isozymes in the Thermotolerant Yeast Kluyveromyces Marxianus and Their Physiological Functions," Bioscience, Biotechnology, and Biochemistry, vol. 71, No. 5, May 2007, pp. 1170-1182.
Kamihara et al., "Temperature Adaptation in Yeast," Department of Industrial Chemistry, Faculty of Engineering, Kyoto University, pp. 773-780, 1992.
Kamihara et al., "Temperature Adaptation in Yeast," Department of Industrial Chemistry, Faculty of Engineering, Kyoto University, pp. 773-780, 1992 (English translation).
Adachi at al., "Purification and Characterization of Particulate Alcohol Dehydrogenase from Gluconobacter Suboxydans," 1978, 42 (11), pp. 2045-2056, Agric. Biol. Chem.
Bergmeryer, "Methods of Enzymic Analysis," Verlag Chemic Weinheim and Academic Press, pp. 444-451, 1974.
O'Donnell, "Fusarium and its Near Relatives," 1993, pp. 225-233, Chapter 24, CAB International, Wallingford.
Kourkoutas et al., "High-Temperature Alcoholic Fermentation of Whey Using Kluyveromyces Marxianus IMB3 Yeast Immobilized on Delignified Cellulosic Material," 2002, 82, pp. 177-181, Bioresource Technology.
Van Der Walt at al., "The Yeasts, A Toxonomic Study, 4th edition," Elsevier, Amsterdam, pp. 77-100, 1998.

*Primary Examiner* — Christian Fronda
(74) *Attorney, Agent, or Firm* — Kenneth H. Sonnenfeld; Margaret B. Brivanlou; King & Spalding

(57) ABSTRACT

The present invention provides a novel yeast strain capable of producing ethanol through fermentation with a high degree of efficiency at a temperature of 37° C. or higher, preferably a temperature ranging from 40 to 49° C. or higher, and also a method for producing ethanol by utilizing the yeast strain, and further, ethanol produced by the method. Therefore, in the present invention, an yeast strain (Deposit No. NITE BP-283, etc) belonging to species *Kluyveromyces marxianus* isolated by a screening step using a culture medium containing sugar in a high concentration and ethanol, is cultured in a culture solution supplemented with 10 to 100 mM of sorbitol at 40 to 49° C.

17 Claims, 8 Drawing Sheets

[Fig. 1]
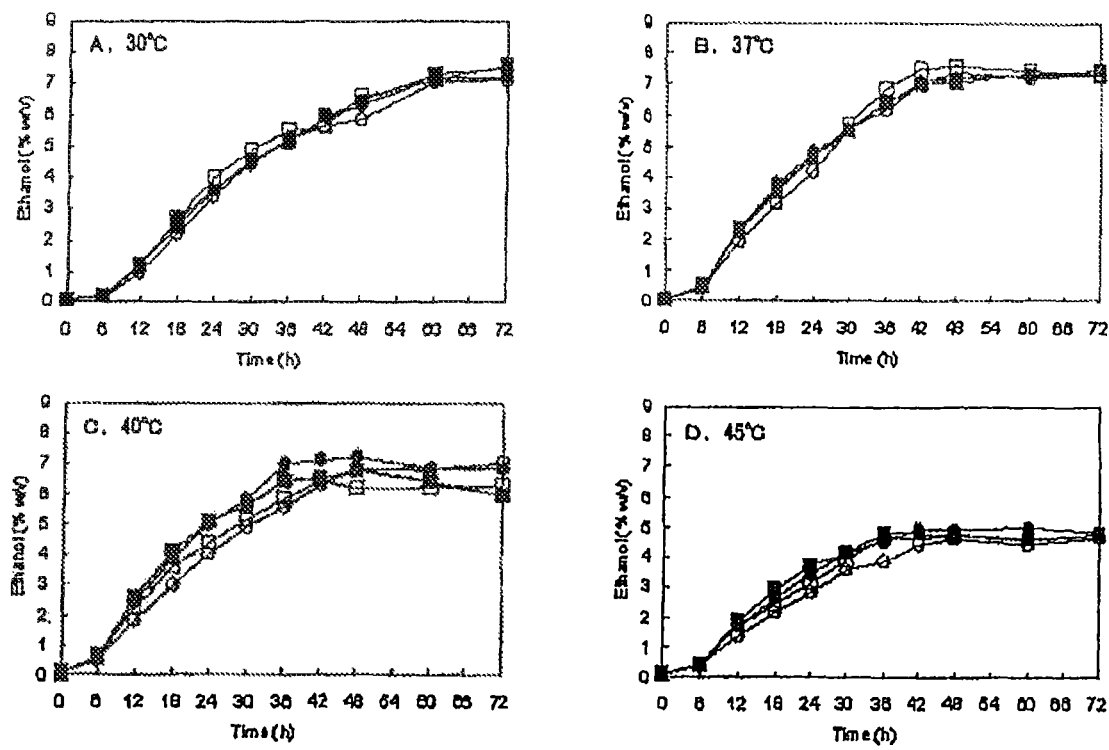
[Fig. 2]
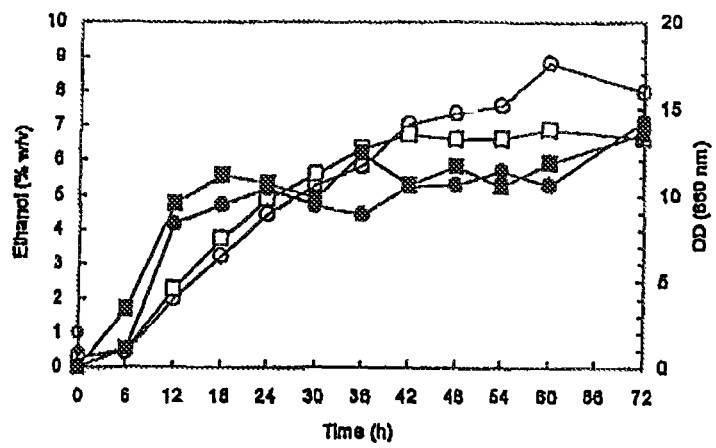

[Fig. 3]
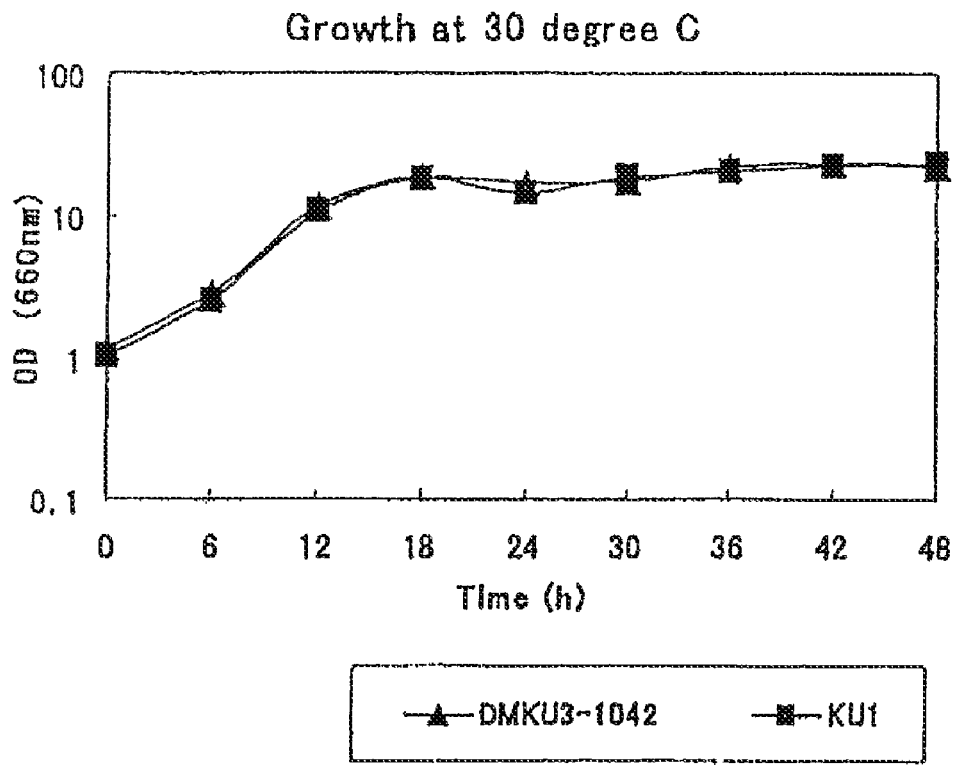
[Fig. 4]
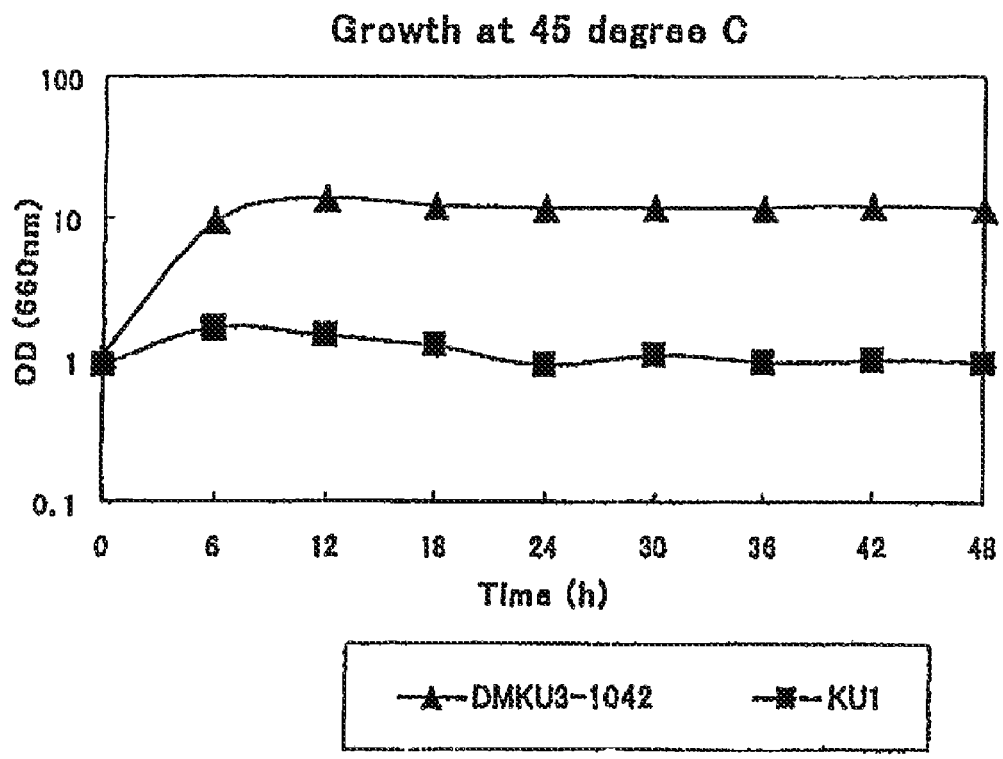

[Fig. 5]
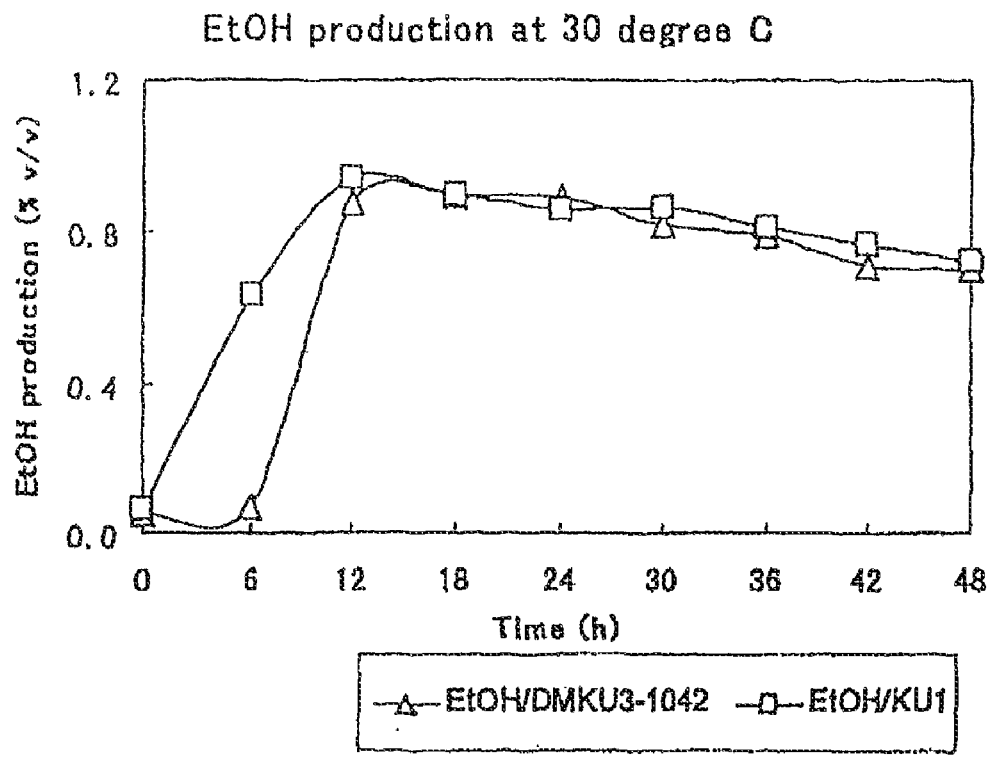
[Fig. 6]
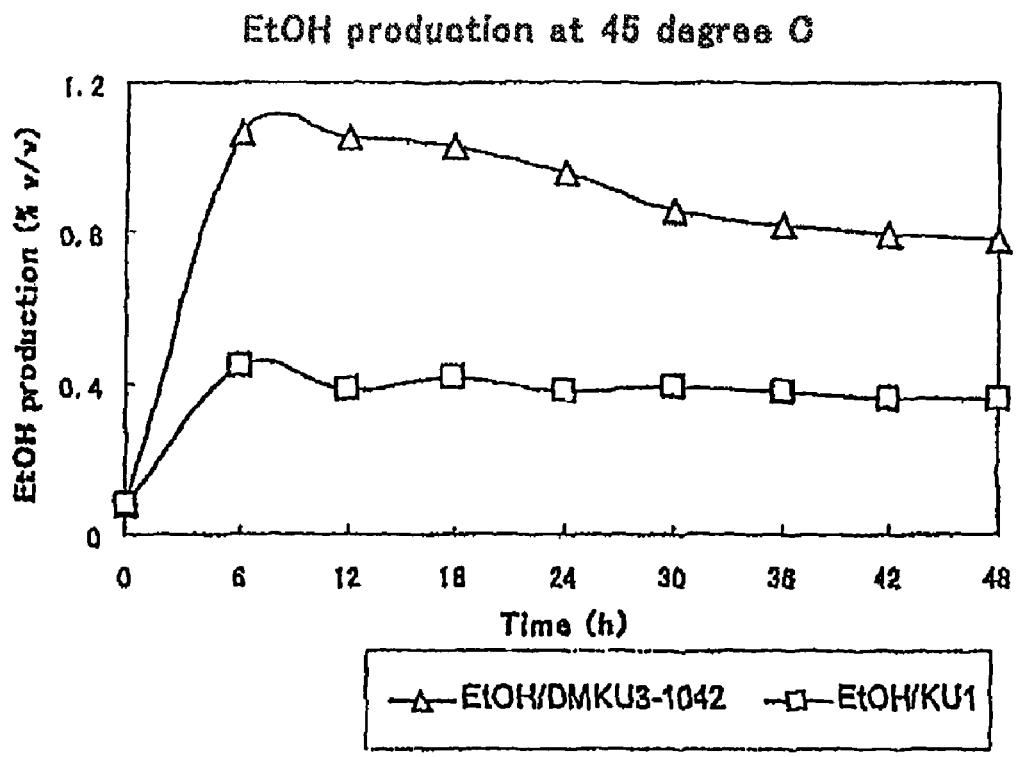

[Fig. 7]
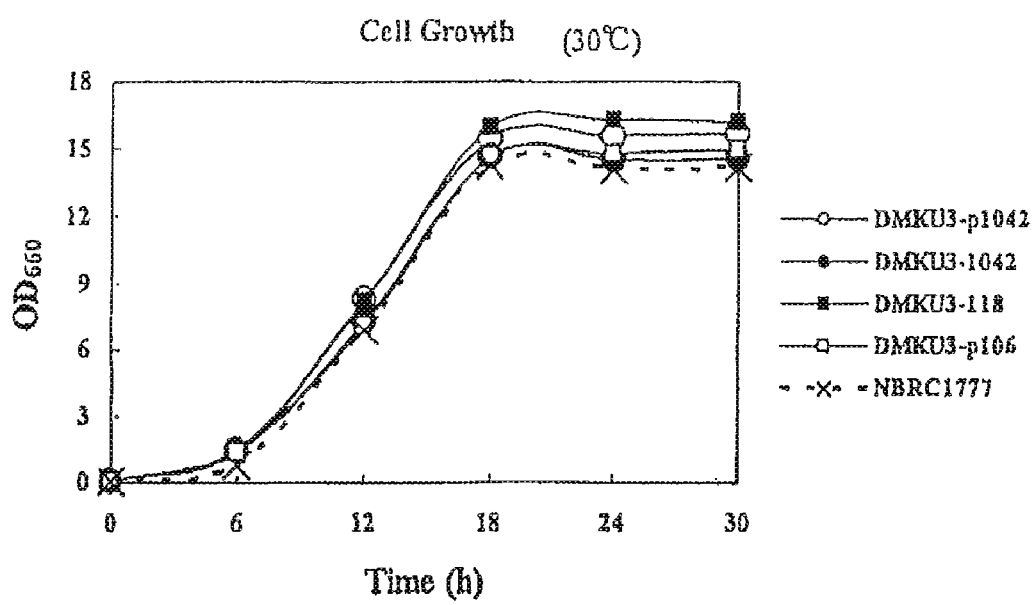
[Fig. 8]
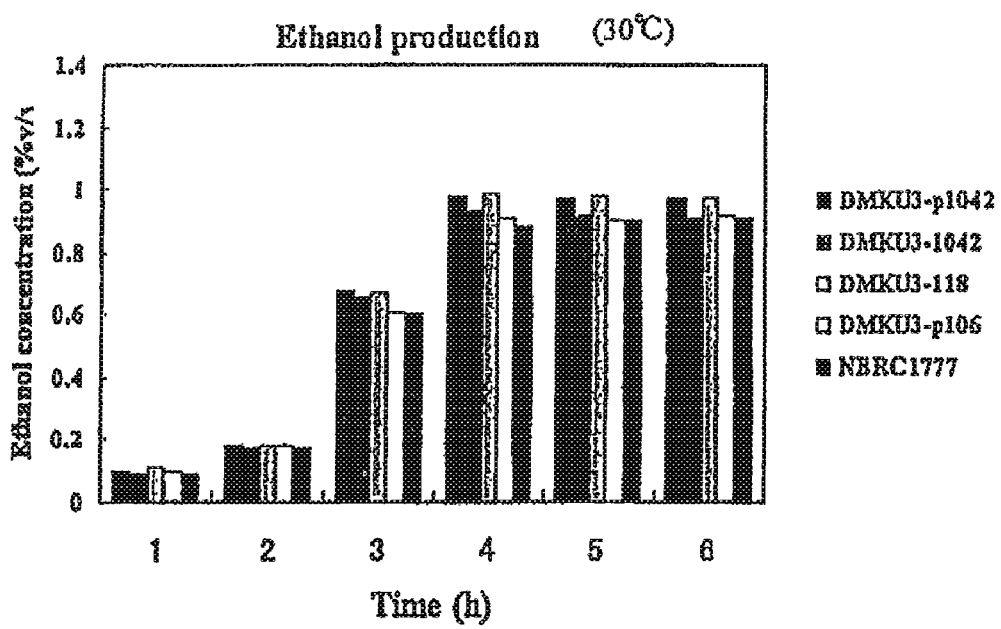

[Fig. 9]
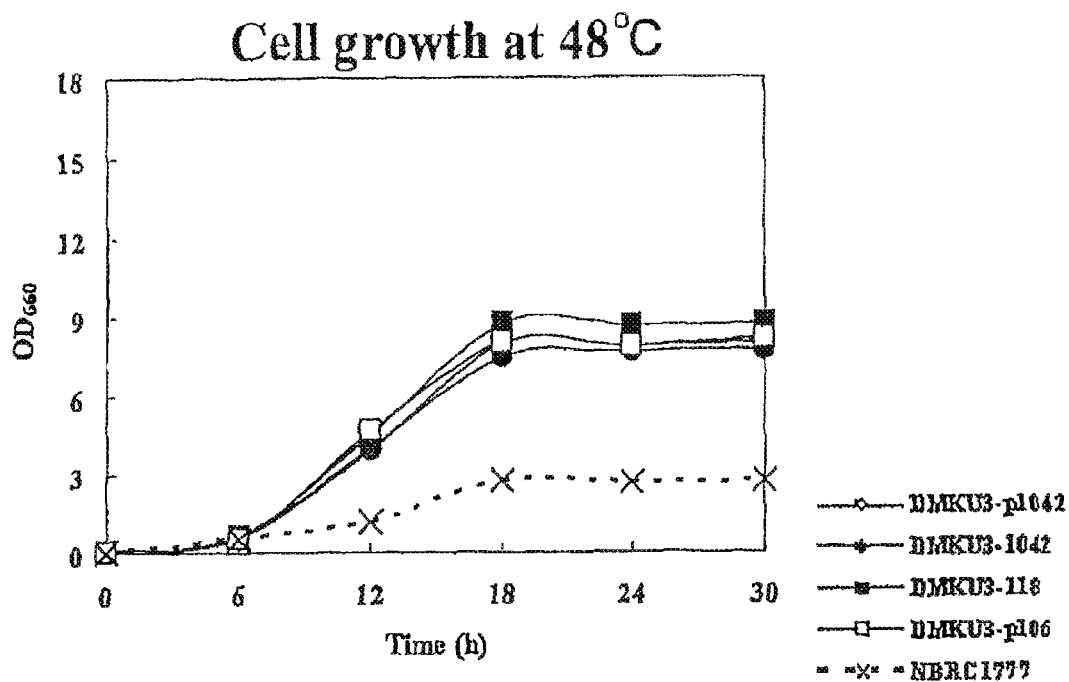
[Fig. 10]
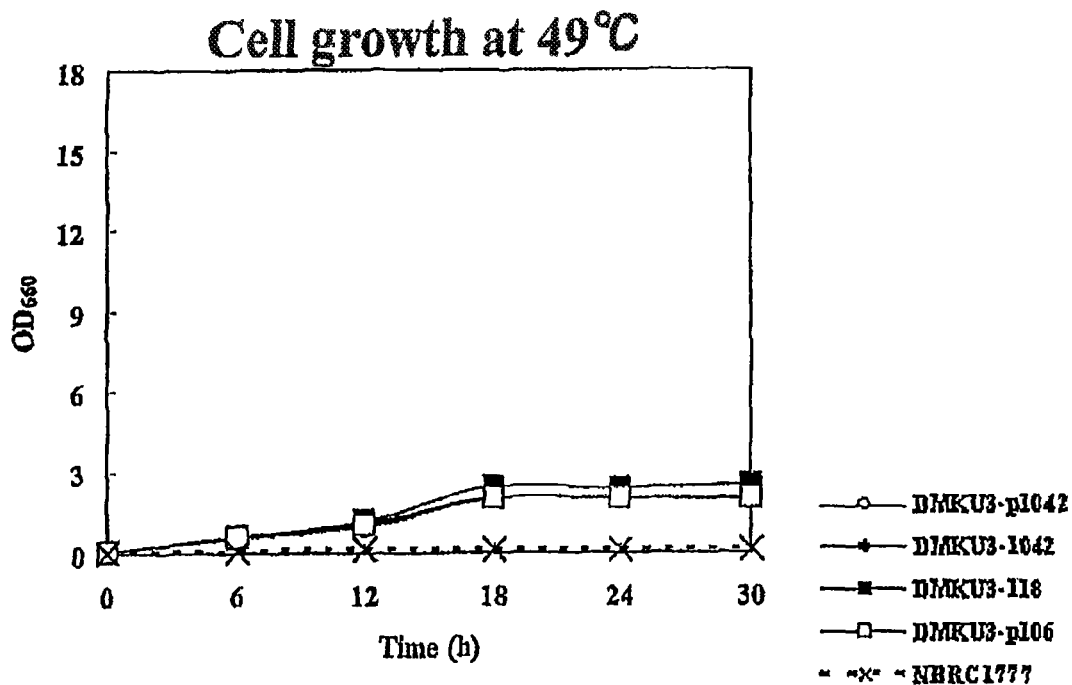

[Fig. 11]
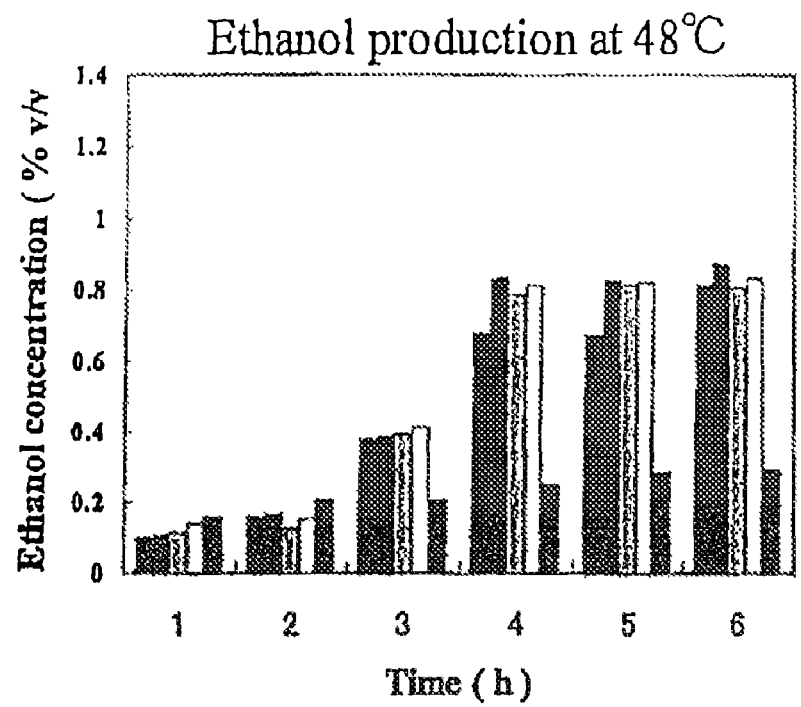
[Fig. 12]
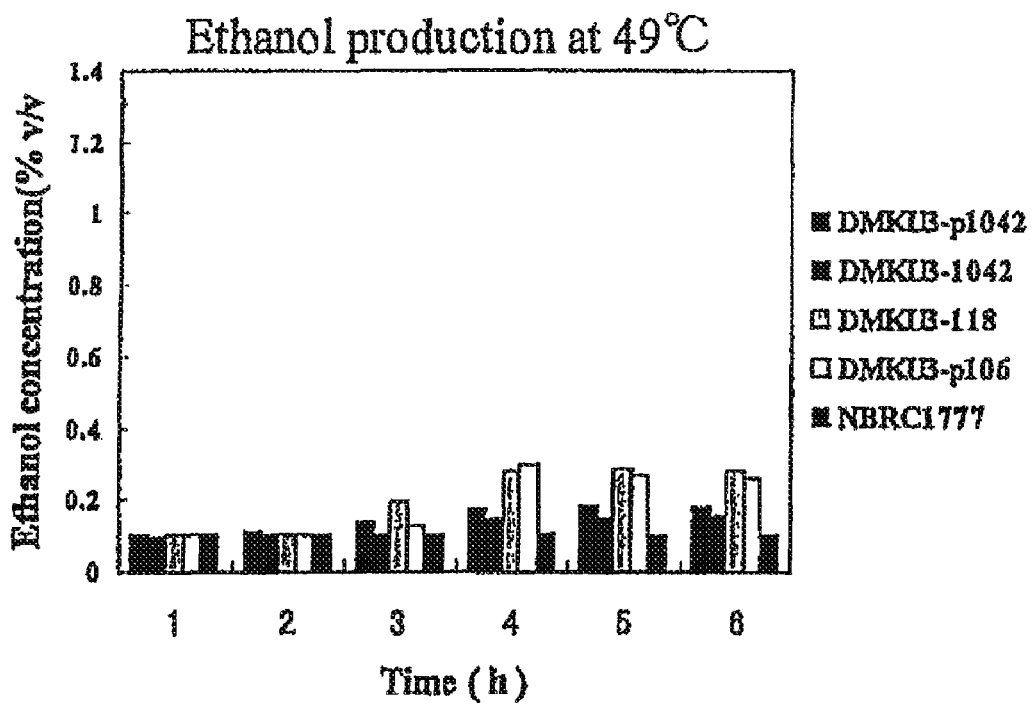

[Fig. 13]
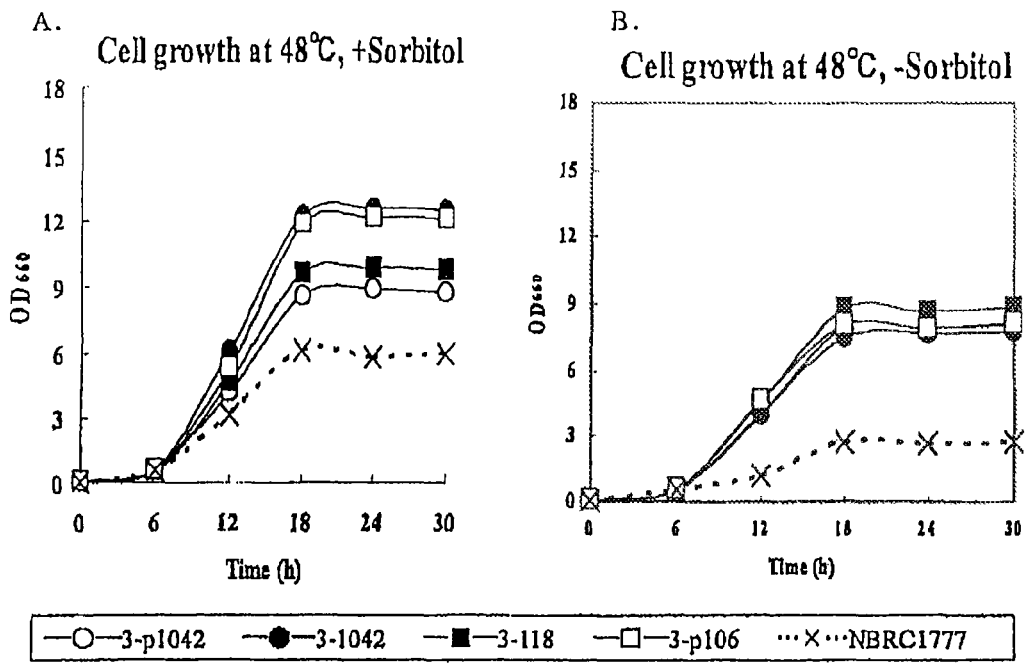
[Fig. 14]
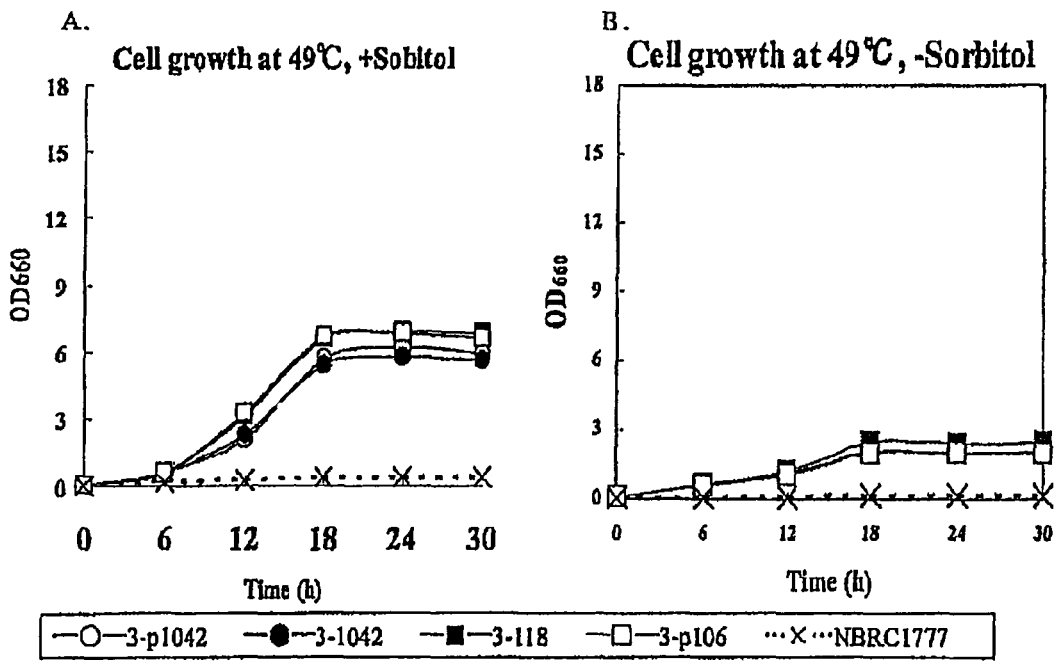

[Fig. 15]
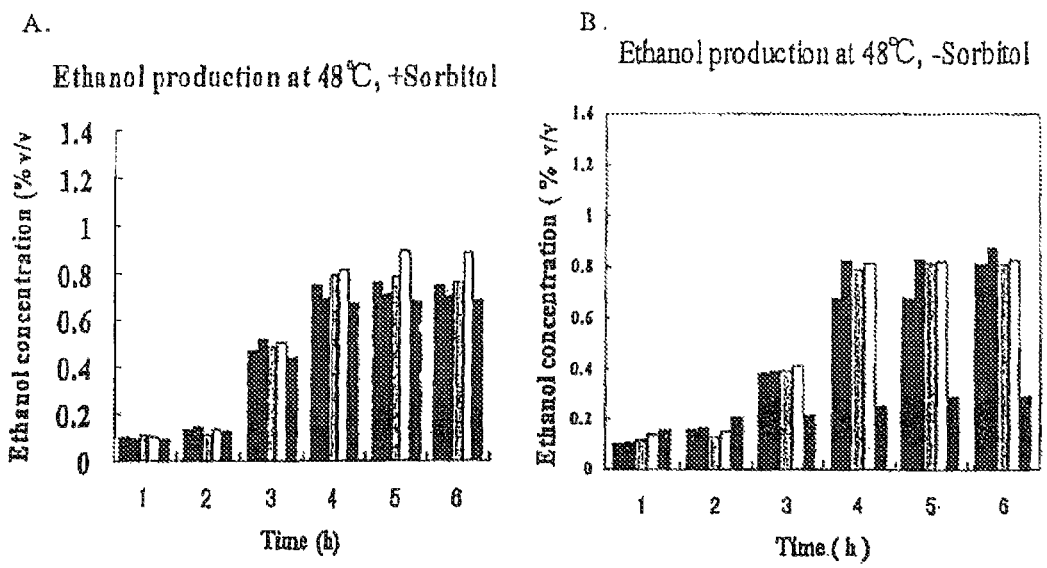
[Fig. 16]
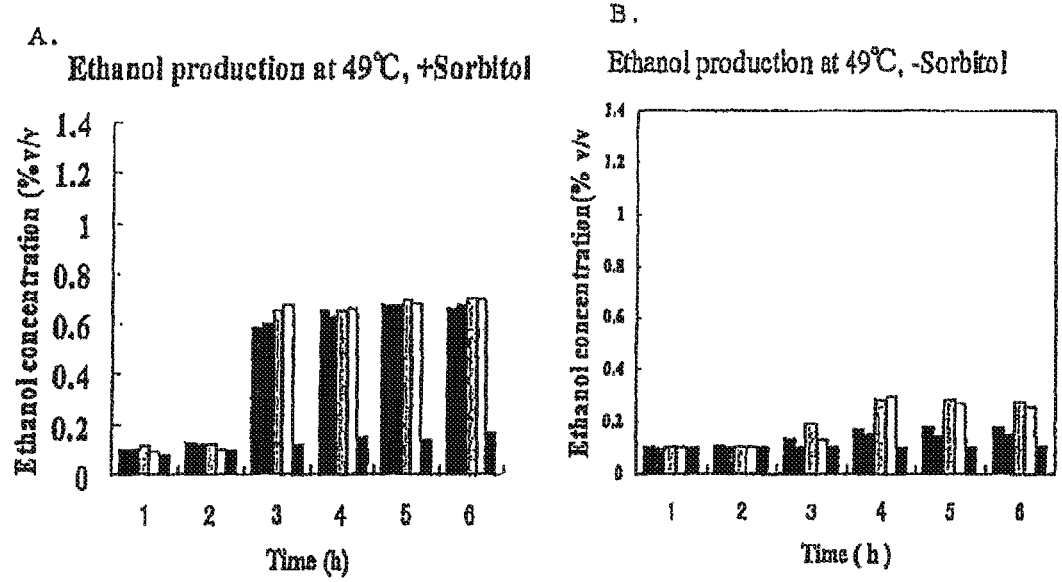

THERMOTOLERANT ETHANOL-PRODUCING YEAST AND ETHANOL PRODUCTION METHOD UTILIZING THE SAME

TECHNICAL FIELD

The present invention relates to a novel microorganism capable of producing ethanol under a high temperature condition and a method for producing ethanol utilizing the same. More specifically, the present invention relates to a strain belonging to species *Kluyveromyces marxianus* which has a thermotolerant ethanol-fermentation ability under a temperature condition of 35° C. or higher and a method for producing ethanol utilizing the same.

BACKGROUND ART

Regardless of whether it is for food use or industrial use, ethanol is a substance that can be used for various applications. Chemically-synthesized ethanol and fermented ethanol by yeast etc. have been used for industrial use and for food use respectively. Especially, recently, because of the development of biotechnology and increasing awareness for biomass utilization, attempts to use fermentative production not only for food use, but also for industrial use, in particular, for fuel ethanol are increasing. The technology of fermentative production using yeast for ethanol production has been used through the ages, and a number of improvements aiming to enhance productivity of yeast which has an important role therein are disclosed.

Use of thermophilic microorganisms can be exemplified as one improvement of fermentative production using microorganism for industrial application. Since generation of heat (fermentation heat) associated with fermentation process reduces life activities such as metabolism of non-thermotolerant microorganism and may lead the microorganism to death, solutions have been taken, for example, by installing a cooling device, in particular, when a large fermenting vessel is used for fermentation. However, cooling devices have drawbacks, such as cost problems etc., and in enzyme chemistry, if fermentation under a high temperature condition is realized, a more effective fermentative production can be expected. Therefore it is effective to isolate a microorganism having both thermotolerance and fermentative ability from nature, or to confer thermotolerance to a fermentative microorganism by genetic recombination. From this viewpoint, various thermotolerant (thermophilic) microorganisms and technology of fermentative production by utilizing the same are disclosed, and examples include a method to confer thermotolerance by introducing a gene of thermophilic methane bacterium, thermophilic bacillus, thermophilic fiber-degrading bacterium, thermophilic thermoactinomyces, or hyperthermophilic archaea into a microorganism of another species; a method for expressing a thermotolerance-related gene of thermophilic bacterium in *Saccharomyces* yeast; and a method for producing ethanol by using *Kluyveromyces marxianus*, a yeast fermentable at high temperature, etc. (Patent Documents 1 to 8). However, the above inventions relate to production of a substance using mainly a thermophilic bacterium, and they had drawbacks, for example, in that the productivity of ethanol is reduced in the case of yeast which thermotolerance is improved. Thus, the development of a thermotolerant microorganism applicable to the technology of fermentative production of ethanol in which exploding demands are predicted hereafter was awaited.

Patent Document 1: Published Japanese translation of PCT international publication No. 2003-520045; "METHOD AND DEVICE FOR PRODUCING BIOGAS, WHICH CONTAINS METHANE, FROM ORGANIC SUBSTANCES"

Patent Document 2: Published Japanese translation of PCT international publication No. 2006-514831; "PREPARATION OF LACTIC ACID FROM A PENTOSE CONTAINING SUBSTRATE"

Patent Document 3: Japanese Laid-Open Patent Application No. 5-336951; "THERMOPHILIC CELLULOSE-DECOMPOSING BACTERIUM"

Patent Document 4: Japanese Laid-Open Patent Application No. 6-303968; "THERMOPHILIC ACTINOMYCES"

Patent Document 5: Japanese Laid-Open Patent Application No. 2000-050894; "A METHOD FOR PRODUCING FERMENTATIVE PRODUCTS AND STRESS-TORELANT MICROORGANISMS"

Patent Document 6: Japanese Laid-Open Patent Application No. 2001-069979; "A METHOD FOR PRODUCING L-GLUTAMINE THROUGH FERMENTATION PROCESS"

Patent Document 7: Japanese Laid-Open Patent Application No. 2006-280253; "A YEAST MUTANT STRAIN CAPABLE OF HIGHLY PRODUCING HEAT-RESISTANT ENZYME"

Patent Document 8: Japanese Laid-Open Patent Application No. 63-42690; "A METHOD FOR PRODUCING ETHANOL USING A YEAST WHICH IS FERMENTATIVE AT HIGH TEMPERATURE"

Non-Patent Document 1: Kourkoutas Y. et al. 2002. Bioresource Technology 82, 177-181.

Non-Patent Document 2: Yarrow D., et al. 1998. The Yeasts, A Taxonomic Study 4th edition. Elsevier, Amsterdam. pp. 77-100.

Non-Patent Document 3: O'Donell K. 1993. Fusarium and its near relatives. CAB International, Wallingford. pp. 225-233.

Non-Patent Document 4: Bergmeryer H. U. 1974. Methods of Enzymic Analysis, Vol. 1. Verlog Chemic Weinheim and Academic Press, New York-London.

Non-Patent Document 5: Adachi et al. 1978. Agric Biol. Chem. 42, 2045-2056.

DISCLOSURE OF THE INVENTION

Object to be Solved by the Present Invention

In view of the above mentioned current situation, the object of the present invention is to provide a novel yeast strain capable of producing effectively ethanol through fermentation even under a temperature condition of 37° C. or higher, preferably a temperature condition of 40 to 45° C. or higher, and a method for producing ethanol by utilizing the yeast strain.

Means to Solve the Object

In order to achieve the above objects, the present inventors have focused on a fermentative microorganism living in tropical areas, and tried a method for isolating a microorganism strain capable of achieving the present objects from the field. Specifically, the present inventors studied the ability of producing ethanol through fermentation of various microorganisms by screening using a medium comprising sugar at a high concentration, and ethanol. Among them, they have found that some strains of a species of yeast, *Kluyveromyces marx-*

*ianus*, have an ability of producing ethanol through fermentation under a temperature condition of 37° C. or higher. Conventionally, microorganisms used for production through fermentation are yeast belonging to the genus *Saccharomyces* (*Saccharomyces cerevisiae*) or fermentative bacterium of the genus *Zymomonas*. However, it is hitherto not known that yeast of the genus *Kluyveromyces* is industrially applicable to produce ethanol through fermentation. Further, the present inventors confirmed that among above the strains, some had an ability of producing ethanol comparable to that of yeast of genus *Saccharomyces*, even at a temperature condition of 35° C. or higher. Particularly, among these yeast strains of the genus *Kluyveromyces*, they have found out DMKU3-1042 strain (Deposit No. NITE BP-283), DMKU3-118 strain (Deposit No. NITE BP-289), DMKU3-p106 strain (Deposit No. NITE BP-290), and DMKU3-p1042 strain (Deposit No. NITE BP-291) which are strains exhibiting a producing ability equal to that of ethanol production of yeast of *Saccharomyces* under optimum conditions, even at a very high temperature condition for fermentation such as 40° C. or higher. The present invention has been thus completed.

Specifically, the present invention relates to (1) a method for producing ethanol comprising culturing a thermotolerant ethanol-producing yeast of species *Kluyveromyces marxianus* having an ethanol fermentation ability at a temperature condition of 35° C. or higher in a culture solution containing sugar alcohol, and (2) the method for producing ethanol according to (1), wherein the sugar alcohol is sorbitol.

Further, the present invention relates to (3) the method for producing ethanol according to (1) or (2), wherein the thermotolerant ethanol-producing yeast has an ethanol fermentation ability under a temperature condition of 40 to 49° C., and (4) the method for producing ethanol according to (3), wherein the thermotolerant ethanol-producing yeast is represented by Deposit No: NITE BP-283, NITE BP-289, NITE BP-290, or NITE BP-291.

Furthermore, the present invention relates to (5) the method for producing ethanol according to any one of (1) to (4), wherein the culture solution contains 15 to 25% sugar; (6) the method for producing ethanol according to any one of (1) to (5), wherein the culture solution comprises 15 to 25% sugar as a main component, and comprises at least one of component selected from 0.01 to 0.5% ammonium salt, 0.01 to 0.5% potassium salt, or 0.01 to 0.5% magnesium salt as an auxiliary component; (7) the method for producing ethanol according to any one of (1) to (5), comprising culturing yeast under a temperature condition of 30 to 40° C., wherein the culture solution comprises 18 to 24% sugar as a main component, and 0.05 to 0.1% ammonium sulfate and 0.025 to 0.1% calcium phosphate as an auxiliary component, and which pH is adjusted from 4.8 to 5.2; and (8) the method for producing ethanol according to any one of (1) to (5), comprising culturing yeast under a temperature condition of 40° C. or higher, wherein the culture solution comprises 16 to 22% sugar as a main component, and 0.05 to 0.1% ammonium sulfate and 0.05 to 0.15% magnesium sulfate as an auxiliary component, and which pH is adjusted from 5.3 to 5.7.

Further, the present invention relates to (9) the method for producing ethanol according to any one of (1) to (8), comprising shaking at 150 to 450 rpm and aerating at 0.1 to 0.3 vvm.

Moreover, the present invention relates to (10) the method for producing ethanol according to any one of (1) to (9), comprising using a culture solution containing 10 to 100 mM of sorbitol.

Furthermore, the present invention relates to (11) the method for producing ethanol according to any one of (1) to (10), wherein a squeezed sugarcane juice is used as a raw material.

Further, the present invention relates to (12) a thermotorelant ethanol-producing yeast of species *Kluyveromyces marxianus* having an ethanol fermentation ability under a temperature condition of 35° C. or higher; (13) the thermotolerant ethanol-producing yeast according to (12) having an ethanol fermentation ability under a temperature condition of 40 to 49° C.; (14) the thermotolerant ethanol-producing yeast according to (13) represented by Deposit No: NITE BP-283, (15) the thermotolerant ethanol-producing yeast according to (13) represented by Deposit No: NITE BP-289; (16) the thermotolerant ethanol-producing yeast according to (13) represented by Deposit No: NITE BP-290; and (17) the thermotolerant ethanol-producing yeast according to (13) represented by Deposit No: NITE BP-291.

Furthermore, the present invention relates to (18) a transformant obtained by modifying or introducing one or more genes in the thermotolerant ethanol-producing yeast according to any one of (14) to (17).

EFFECT OF THE PRESENT INVENTION

By utilizing a thermotolerant ethanol-producing yeast provided by the present invention, ethanol can be produced effectively regardless of whether it is for food application or industrial application. In particular, since the yeast provided by the present invention has an ability to produce ethanol through fermentation effectively even under a high temperature condition of 40° C. to 45° C., a device for fermentation-heat removal used in the conventional production of ethanol through fermentation using yeast would be downsized or unnecessary, and the fermenter facilities could be simplified and enlarged. Therefore, cost of facilities can be reduced and production efficiency can be improved. Thus, it is expected that a large-scale production of ethanol through fermentation for fuel application using biomass such as sugarcane as a raw material can be readily conducted.

BRIEF DESCRIPTION OF DRAWINGS

FIG. 1 shows changes of the ethanol concentration (vertical axis: %, w/v) over time (horizontal axis; time from the initiation of the culture) in a culture solution at different culture temperatures for 4 strains of thermotolerant ethanol-producing yeast isolated from the field.

FIG. 2 shows changes over time (horizontal axis; time) of ethanol concentration and yeast growth of the DMKU3-1042 strain during the culture step under different temperature conditions.

FIG. 3 shows the growth of the 3-1042 strain and a standard strain of *Saccharomyces cerevisiae* (KU1 strain) at 30° C. by comparison. Vertical axis shows an OD660 value, and horizontal axis shows the time (hour) from the initiation of the culture.

FIG. 4 shows the growth of the 3-1042 strain and the KU1 strain at 45° C. by comparison. Vertical axis shows an OD660 value, and horizontal axis shows the time from the initiation of the culture.

FIG. 5 shows the ethanol-producing ability of the 3-1042 strain and the KU1 strain at 30° C. by comparison. Vertical axis shows ethanol concentration (%, v/v) in a culture solution, and horizontal axis shows the time from the initiation of the culture.

FIG. 6 shows the ethanol-producing ability of the 3-1042 strain and the KU1 strain at 45° C. by comparison. Vertical axis shows the ethanol concentration (%, v/v) in a culture solution, and horizontal axis shows the time from the initiation of the culture.

FIG. 7 shows the growth ability of the 4 strains of thermotolerant ethanol-producing yeast of the present invention (3-p1042, 3-1042, 3-118, 3-p106) and a standard strain of *K. marxianus* yeast (NBRC1777) under a culture condition of 30° C. by comparison. Vertical axis shows an OD660 value, and horizontal axis shows the time (h) from the initiation of the culture.

FIG. 8 shows the ethanol-producing ability of the 4 strains of thermotolerant ethanol-producing yeast of the present invention and a normal strain under a culture condition of 30° C. by comparison. Vertical axis shows the ethanol concentration (%, v/v), and horizontal axis shows the time (h) from the initiation of the culture.

FIG. 9 shows the ethanol-producing ability of the 4 strains of thermotolerant ethanol-producing yeast of the present invention and a standard strain under a culture condition of 48° C. by comparison.

FIG. 10 shows the ethanol-producing ability of the 4 strains of thermotolerant ethanol-producing yeast of the present invention and a standard strain under a culture condition of 49° C. by comparison.

FIG. 11 shows the ethanol-producing ability of the 4 strains of thermotolerant ethanol-producing yeast of the present invention and a standard strain under a culture condition of 48° C. by comparison.

FIG. 12 shows the ethanol-producing ability of the 4 strains of thermotolerant ethanol-producing yeast of the present invention and a standard strain under a culture condition of 49° C. by comparison.

FIG. 13 shows the influence of sorbitol addition on growth under a culture condition of 48° C. (A) shows the results with sorbitol and (B) shows the results without sorbitol.

FIG. 14 shows the influence of sorbitol addition on growth under a culture condition of 49° C. (A) shows the results with sorbitol and (B) shows the results without sorbitol.

FIG. 15 shows the influence of sorbitol addition on ethanol-producing ability under a culture condition of 48° C. (A) shows the results with sorbitol and (B) shows the results without solbitol.

FIG. 16 shows the influence of sorbitol addition on ethanol-producing ability under a culture condition of 49° C. (A) shows the results with sorbitol and (B) shows the results without sorbitol.

BEST MODE OF CARRYING OUT THE INVENTION

The best mode of carrying out the present invention is hereinafter described. The first embodiment of the present invention is to provide a thermotolerant ethanol-producing yeast of species *Kluyveromyces marxianus* having an ethanol fermentation ability under a temperature condition of 35° C. or higher. Conventionally, yeast of the genus *Saccharomyces* were mainly used for producing ethanol through fermentation, and improved technologies using genetic engineering procedure also focused on these *Saccharomyces* yeasts. Moreover, as it has been considered that a suitable temperature for fermentation is approximately from room temperature to 30° C., an equipment for cooling to keep a fermenter at a suitable temperature was often required in the conventional ethanol fermentation industry. Yeast of the genus *Kluyveromyces* have been hitherto utilized in the high-temperature fermentation using lignin-cellulosic materials, or as a "killer yeast" to inhibit growth of other species of yeast, or for lactic acid fermentation, etc. (Non-Patent document 1). The present invention newly provides an yeast strain of species *Kluyveromyces marxianus* capable of producing ethanol which is applicable to fuel application etc. from raw materials such as squeezed sugarcane juice. The origin of the yeast strain of species *Kluyveromyces marxianus* of the present invention is not limited as long as it is a strain having ethanol fermentation ability under a temperature condition of 35° C. or higher, preferably ranging from 40 to 49° C. However, a yeast strain which has been screened through 2 steps, including (a) a step of culturing by using a medium containing 5 to 10% sugar, 0.01 to 0.1% ammonium sulfate, and 2 to 5% ethanol under a temperature condition of 30 to 37° C.; (b) a step of culturing the yeast strain which has proliferated in the step (a) by using a medium containing 5 to 10% sugar, 0.01 to 0.1% ammonium sulfate, and 2 to 5% ethanol under a temperature condition of 40 to 45° C. The above screening step comprises to suspend for example a soil sample in water, inoculate the sample on a medium, such as liquid medium or agar medium, containing the components of (a) and culture the same under a temperature condition of 35° C. Further, the strains which have been proliferated are inoculated on a medium, such as an agar medium, containing the components of (b) and cultured under a temperature condition of 40 to 45° C. to obtain a desired strain as a colony. In step (a), ethanol tolerance is selected, and in step (b), the termotolerance at a temperature of 40 to 45° C. is selected. A yeast strain satisfying all of the above conditions can be preferably exemplified as follows: *Kluyveromyces marxianus* DMKU3-1042 strain (Deposit No. NITE BP-283), DMKU3-118 strain (Deposit No. NITE BP-289), DMKU3-p106 strain (Deposit No. NITE BP-290), and DMKU3-p1042 strain (Deposit No. NITE BP-291). Those strains have been deposited at Incorporated Administrative Agency, National Institute of Technology and Evaluation (NITE), NITE Patent Microorganisms Depositary (2-5-8, Kazusakamatari, Kisarazu-shi, Chiba, 292-0818, Japan) under the Budapest Treaty.

Strains of *Kluyveromyces marxianus* (DMKU3-1042 strain, 3-118, 3-p106, and 3-p1042) provided by the present invention have been isolated from nature as a strain having an ethanol fermentation ability under a high temperature condition. However, modification of genes of the present strains related to, for example ethanol fermentation or thermotolerance by using genetic engineering, or breed improvement comprising introducing genes derived from other microorganisms into the present strain in order to further confer useful properties, are also advantageous. As a technology for genetic modification or introduction, procedures normally used in the field of genetic engineering using microorganisms may be appropriately applied. Examples include, without limiting the present invention, modification of genomic genes by homologous recombination and introduction of a novel gene (a group of genes) using a plasmid vector.

Further, the present invention provides a method for producing ethanol by utilizing the thermotolerant ethanol-producing yeast of the present invention described above in the presence of sugar alcohol. More specifically, the method for producing ethanol of the present invention is not particularly limited as long as it is a method comprising culturing a thermotolerant ethanol-producing yeast of species *Kluyveromyces marxianus* having an ethanol fermentation ability at a temperature condition of 35° C. or higher in a culture solution containing sugar alcohol. Since the fundamental principle of ethanol fermentation of anaerobic glycolysis remains the same even when the yeast strains provided by the present invention are utilized, in the production of ethanol through fermentation by utilizing the yeast of the present invention, it is possible to conduct fermentation by adding the ethanol-producing yeast of the above embodiment into a stock solution containing a proper amount of sugar (carbon hydride) as main component, and preferably containing a nitrogen source, a potassium source, and trace metals such as magnesium as auxiliary components. For a device, an equipment, and a composition of the raw material liquid etc. used for fermentation, those used in the field of fermentation industry may be appropriately applied. A preferred example include a method for producing ethanol using a culture solution containing 15 to 20% sugar as a main component and sugar alcohol as an essential component, and preferably, further comprising at least one component selected from 0.01 to 0.5% ammonium salt, 0.01 to 0.5% potassium salt, and 0.01 to 0.5% magnesium salt as an auxiliary component in addition to the above ingredients, without limiting the present invention.

As described in the Examples in the following, the thermotolerant ethanol-producing yeast provided by the present invention has a feature that the preferred composition of culture solution varies depending on the temperature conditions. Therefore, in the production of ethanol under a temperature condition between 30 to 40° C., in particular, under a temperature condition of approximately 37° C., it is advantageous to use a culture solution containing 20 to 24% of sugar as a main component, 0.05 to 0.1% of ammonium sulfate and 0.025 to 0.1% of calcium phosphate as an auxiliary component, which pH is controlled from 4.8 to 5.2. On the other hand, in the production of ethanol under a temperature condition of 40° C. or higher, it is advantageous to use a culture solution containing 20 to 24% sugar as a main component, 0.05 to 0.1% ammonium sulfate and 0.05 to 0.2%, more preferably 0.15% magnesium sulfate as an auxiliary component, which pH is controlled from 5.3 to 5.7.

Further, in ethanol fermentation using the thermotolerant ethanol-producing yeast provided by the present invention, it is advantageous to conduct fermentation by applying shaking corresponding to 150 to 450 rpm (Round per minute), preferably 300 rpm, and aeration corresponding to 0.1 to 0.3 vvm (Vessel volume per minute), preferably 0.2 vvm to increase efficiency of fermentation. In particular, aeration is extremely effective to increase cell density of yeast in a mass culture system as described in the following Examples.

In the method for producing ethanol according to the present invention, as described above, sugar alcohol is required as an essential component of a culture solution to improve growth ability and ethanol-producing ability of the thermotolerant ethanol-producing yeast under a high temperature condition. Examples of sugar alcohol include: erythritol, glycerin, HSH, isomalt, lactitol, maltitol, mannitol, sorbitol, xylitol, reduced palatinose, xylobiitol, and cellobitol. Particularly, sorbitol can be preferably exemplified. Sorbitol is a kind of sugar alcohol highly contained in fruits such as apple and pear, and it is known that sorbitol does not easily ferment compared to other sugars, prevents fat from oxidizing, and stabilizes protein. The high temperature condition of 40° C. or higher is also a severe environment for the thermotolerant ethanol-producing yeast, and it is considered that these properties of sorbitol assist yeast growth and ethanol production. It is effective to culture in a medium containing sugar alcohol at a concentration within a range of 10 to 100 mM, more preferably sugar alcohol at a concentration in the vicinity of 50 mM, e.g. in a medium containing sorbitol at a concentration within a range of 10 to 100 mM, more preferably sorbitol at a concentration in the vicinity of 50 mM. As described in the following Example, it has been demonstrated that ethanol production can be conducted even under a severe environment of 48° C. and 49° C. by adding sorbitol. In particular, at a temperature of 49° C., no effect was observed in a standard yeast strain of species *K. marxianus*, whereas it was shown that growth ability and ethanol-producing ability were both significantly improved in the strains of thermotolerant ethanol-producing yeast of the present invention. Therefore, the addition of the present auxiliary component is highly effective.

In the ethanol fermentation production using the thermotolerant ethanol-producing yeast provided by the present invention, as sugar which is a main component contained in the stock solution, the following can be used: pure sugar such as glucose, sucrose, and fructose, and a mixture thereof, a plant material which is used as a material for alcohols, e.g. various raw materials which are generically termed as biomass such as kinds of rice, oats, potatoes, sugarcane, sugar maple, sugar beet, and corn. Among these, those containing monosaccharide and oligosaccharide, the squeezed juice etc. thereof can be used per se, and those mainly containing polysaccharide such as starch and cellulose, it is preferred that hydrolysis of polysaccharide is conducted by a microorganism having an enzyme that can degrade these polysaccharides or having a degradation ability of these polysaccharides to degrade up to monosaccharide or oligosaccharide for use. It is estimated that demands of "bioethanol" produced from biomass raw materials will be hereafter increased as an alternative fuel to oil resources. Thus, it is expected that the use of the thermotolerant ethanol-producing yeast provided by the present invention and ethanol produced by the yeast will contribute to the bioethanol related industries. As described above, various biomass can be used as raw materials of bioethanol, and among these materials, in particular, "sugarcane juice" which is a residue after refining sugar from sugarcane is a preferred raw material since sugarcane juice is only used for animal feeding stuff etc. at present, and contains highly-concentrated sugar. Examples of the present invention are described in the following, while the present invention is not limited to these examples.

EXAMPLE 1

(Isolation of a Thermotolerant Microorganism from the Field)

Soil samples and water samples were collected from sugarcane plantations and sugar refining factories in 4 regions of Kingdom of Thailand, i.e. Phra NakhonSi Ayutthaya, Ratchaburi, Suphanburi, and Uthaithani. These samples were added into a sugarcane juice culture solution (5 to 8% total sugars) containing 0.05% ammonium sulfate and 4% ethanol (v/v), and the mixture was cultured in a shaking apparatus (Gallenkamp Orbital Incubator, Leicester, UK) at 170 rpm under a temperature condition of 35° C., for 3 days. 3 days later, a portion of the culture solution (including microorganisms) was inoculated on an agar medium having the same composition and cultured at 35° C. 72 colonies of yeast which have appeared on the agar medium were picked up and transferred on a YPD agar medium (1% yeast extract, 2% peptone, 2% glucose, 2% agar), and stored at 8° C.

(Screening of Thermotolerant Yeasts)

Thermotolerant ethanol-producing strains were screened by the following method from the above 72 strains. Firstly, colonies on the YPD agar medium were picked up and inoculated in 50 ml of a sugarcane juice culture solution (total sugar concentration 2%; containing 0.05% ammonium sulfate; pH adjusted to 4.5 with 1 N hydrochloric acid) in a conical flask, and cultured by shaking for 24 hours under a temperature condition of 25 to 28° C. Approximately 5 ml of the culture solution obtained herein was transferred into 100 ml of sugarcane juice culture solution for screening (sucrose was added and total sugar concentration was adjusted to 18%; containing 0.05% ammonium sulfate; pH adjusted to 4.5 with 1N hydrochloric acid) in a conical flask, and cultured by shaking under a temperature condition of 40° C. or 45° C. and the growth was observed. Among the 72 strains, growth was observed in 55 strains at 40° C., and 37 strains out of these, growth was observed even at 45° C. In order to examine the ethanol-producing ability of these 55 strains, culture was conducted for 72 hours under a temperature condition of 37° C. and 40° C. to measure the ethanol concentration contained in the culture solution. As a result, it was found that 4 strains, DMKU3-1042, DMKU3-118, DMKU3-p106, and DMKU3-p1042 have a high level of ethanol-producing ability (hereinafter, name of strains will be described by omitting DMKU accordingly). The ethanol-producing ability of these 4 strains at each temperature is shown in Table 1 below, and the ethanol-producing ability is represented by the ethanol concentration (%, w/v) contained in a culture solution. Since the remaining 51 strains showed a far lower level of ethanol-producing ability compared to these 4 strains, analysis hereinafter was conducted for these 4 strains.

TABLE 1

Ethanol-producing ability of 4 strains of *K. marxianus*

| | Ethanol concentration in a culture solution (%, w/v) | |
|---|---|---|
| | 37° C. | 40° C. |
| DMKU3-1042 | 6.78 | 6.17 |
| DMKU3-118 | 6.57 | 5.58 |
| DMKU3-p106 | 6.50 | 5.14 |
| DMKU3-p1042 | 6.38 | 6.33 |

(Identification of Yeast)

Morphological, physiological and biochemical properties of the 4 strains obtained through the above screening were identified by the method of Yarrow (Non-Patent Document 2). Further, genomic DNAs were extracted from these yeasts, D1/D2 region of Large subunit rDNA was amplified by using a primer developed by O'Donnell (Non-Patent Document 3), nucleotide (base) sequences thereof were determined by an ABI PRISM 3100 sequencer (Applied Biosystem, USA), and compared with known species of yeast by using BLAST homology search. As a result of the above, specifically, since the nucleotide sequence of D1/D2 region were identical to the sequence of a kind of yeast *Kluyveromyces marxianus*, all of the 4 yeast strains were classified as *K. marxianus*.

EXAMPLE 2

(Examination of Ethanol-producing Ability—200 ml Scale)

The ethanol-producing ability of the above 55 strains was investigated in a 500 ml size flask, firstly, for the temperature condition by using 200 ml of sugarcane juice culture solution (total sugar concentration 8%; ammonium sulfate concentration 0.05%; pH 4.5). The yeast strains were inoculated in the culture solution and cultured by shaking at 110 strokes/min using Reciprocating water bath shaker (Model R76, New Brunswick Scientific, USA).

FIG. 1 shows the ethanol-producing ability of these 4 strains under respective temperature conditions. Each graph shows the ethanol-producing ability of each strain (DMKU3-p1042=○; DMKU3-1042=●; DMKU3-p106=□; DMKU3-118=■) at 30° C., 37° C., 40° C., and 45° C., respectively, and the change of ethanol concentration (vertical axis; %, w/v) in the culture solution over time is shown (horizontal axis; time from the initiation of the culture). The condition of the culture solution was as follows: total sugar concentration 18%, ammonium sulfate concentration 0.05%, and pH 4.5 (not containing phosphoric acid-potassium and magnesium sulfate). The maximum ethanol concentration of 4 strains at 30° C. and 37° C. (graph A and B) was 7.13 to 7.6% (w/v), among which the ethanol concentration of the 3-118 strain and 3-1042 strain were almost the same at 30° C. and 37° C. However, the ethanol concentration of the 3-p106 strain and 3-p1042 strain was higher at 37° C.

For the ethanol concentration after 48 hours at 40° C. (graph C), the 3-1042 strain showed the highest value of 7.23%, and moreover, this value was by no means inferior to that of 7.43% at 37° C. Further, this value was reflected to the ethanol productivity in 1 l (liter) per hour (expressed by g/l·h), and the productivity at 37° C. was 1.03 g/l·h, whereas the productivity at 40° C. indicated a high value of 1.51 g/l·h. The ethanol concentration of the other 3 strains after 48 hours was 6.43 to 6.85%.

There was a tendency that the ethanol-producing ability of each strain at 45° C. (graph D) was lower compared to the ethanol-producing ability at 40° C. The 3-1042 strain showed the highest value among the 4 strains similarly as at 40° C., and the ethanol concentration was 4.93%, and the productivity was 1.17 g/l·h. Further, it was found that, at 40° C. and 45° C., the time when the ethanol concentration became maximum was shifted to be earlier (36 to 48 hours) compared to at 30° C. and 37° C. It was decided that this DMKU3-1042 strain would be used in the following examination for a composition of a culture solution and ethanol productivity in a large scale. Table 2 below shows the ethanol concentration and productivity of the 4 strains under respective temperature conditions.

TABLE 2

Comparison of ethanol-producing ability of each strain under each temperature condition

| | 30° C. | | 37° C. | | 40° C. | | 45° C. | |
|---|---|---|---|---|---|---|---|---|
| | Ethanol % (w/v) | Product*[1] g/l·h | Ethanol % (w/v) | Product* g/l·h | Ethanol % (w/v) | Product* g/l·h | Ethanol % (w/v) | Product* g/l·h |
| 3-p106 | 7.60 (72 h*[2]) | 1.06 | 7.56 (48 h) | 1.57 | 6.43 (42 h) | 1.51 | 4.74 (48 h) | 0.99 |
| 3-118 | 7.48 (72 h) | 1.04 | 7.42 (72 h) | 1.03 | 6.78 (48 h) | 1.41 | 4.78 (36 h) | 1.33 |

TABLE 2-continued

Comparison of ethanol-producing ability of each strain under each temperature condition

|  | 30° C. | | 37° C. | | 40° C. | | 45° C. | |
| --- | --- | --- | --- | --- | --- | --- | --- | --- |
|  | Ethanol % (w/v) | Product*[1] g/l·h | Ethanol % (w/v) | Product* g/l·h | Ethanol % (w/v) | Product* g/l·h | Ethanol % (w/v) | Product* g/l·h |
| 3-1042 | 7.21 (72 h) | 1.00 | 7.43 (72 h) | 1.03 | 7.23 (48 h) | 1.51 | 4.93 (42 h) | 1.17 |
| 3-p1042 | 7.13 (72 h) | 0.99 | 7.39 (48 h) | 1.54 | 6.84 (48 h) | 1.43 | 4.59 (48 h) | 0.96 |

*[1]Productivity,
*[2]Time recorded the maximum value (upper line) of the ethanol concentration In order to optimize the sugarcane juice culture solution by using the 3-1042 strain which was most superior in ethanol-producing ability at 40° C. and 45° C., the following sugarcane juice culture solutions were prepared: 5 variations of total sugar concentration: 16%, 18%, 20%, 22% and 24%; 4 variations of ammonium sulfate concentration: 0%, 0.05%, 0.07%, and 0.1%; 4 variations of phosphoric acid-potassium concentration: 0%, 0.025%, 0.05% and 0.1%; 6 variations of magnesium sulfate heptahydrate concentration: 0%, 0.05%, 0.1%, 0.15%, 0.2% and 0.3%; 4 variations of pH: 4.0, 4.5, 5.0 and 5.5. And then, the ethanol-producing ability and the effect of each component at 37° C. and 40° C. were compared and examined.

With respect to the total sugar concentration, the final concentration of ethanol was increased compared to the sugar concentration at both 37° C. and 40° C., and reached the maximum level at 22%. However, since the final ethanol concentration was declined at 24%, it was considered that the optimum sugar concentration was around 22%. With a sugar concentration of 22%, the ethanol concentration after 54 hours was 8.29%, the ethanol productivity was 1.54 g/l·h, and the yield (rate to a theoretical value estimated from the sugar concentration) was 73.9% at 37° C. With a sugar concentration of 22%, the ethanol concentration reached a maximum level (6.88%) at 40° C., and time to reach the maximum level was shorter than the one at 37° C., however, the maximum productivity (1.42%/l·h) and yield (72.6%) were recorded with a sugar concentration of 16%.

In order to examine the influence of a nitrogen source on ethanol production, 4 types of culture solutions containing 0 to 0.1% ammonium sulfate in a syrup culture stock solution with a total sugar concentration of 22%, pH 4.5, were prepared in which the 3-1042 strain was cultured. At 37° C., the maximum level of ethanol concentration which was 7.8% was recorded with an ammonium sulfate concentration of 0.07%, the productivity herein was 1.08 g/l·h, and the yield was 69.5%. However, the productivity was higher with an ammonium sulfate concentration of 0.05%, which level was 1.36 g/l·h. The yield herein was 65.5% and the ethanol concentration was 7.35%. In both cases, the levels were higher compared to when not adding ammonium sulfate (0%), where the ethanol concentration was 6.85%, the productivity was 0.95 g/l·h, and the yield was 61.0%. Therefore, it has been revealed that it was effective to add ammonium sulfate as a nitrogen source. At 40° C., the ethanol concentration when ammonium sulfate is added was higher compared to the ethanol concentration (6.22%) when ammonium sulfate is not added, and in particular, the level was excellent when adding 0.05% of ammonium sulfate. When 0.05% ammonium sulfate was added, the ethanol concentration was 6.60%, the productivity was 1.37 g/l·h, and the yield was 58.8%, and the levels were higher compared to when not adding ammonium sulfate, where productivity was 1.15 g/l·h and the yield was 55.4%. From these results, it has been revealed that it was also effective to add an appropriate amount of ammonium sulfate at 40° C.

In order to examine the influence of a potassium source on ethanol production, 4 types of culture solutions containing 0 to 0.1% of phosphoric acid-potassium in a syrup culture stock solution with a total sugar concentration of 22%, an ammonium sulfate concentration of 0.05%, pH 4.5, in which the 3-1042 strain was cultured. At 37° C., the levels were higher when phosphoric acid-potassium was added compared when not adding phosphoric acid-potassium (ethanol concentration 6.92%; productivity 0.96 g/l·h; and yield 61.7%). In particular, when 0.05% was added, the maximum level was recorded (ethanol concentration 7.65%; productivity 1.06 g/l·h; yield 68.1%). On the contrary, at 40° C., no improvement by adding phosphoric acid-potassium was observed. From these results, it has been revealed that it was effective to add an appropriate amount of potassium source (phosphoric acid-potassium) was effective in the ethanol production using the yeasts provided by the present invention at 37° C. or lower.

In order to examine the influence of a magnesium source on ethanol production, 6 types of culture solutions containing 0 to 0.3% of magnesium sulfate heptahydrate in a syrup culture stock solution with a total sugar concentration of 22%, ammonium sulfate concentration of 0.05%, phosphoric acid-potassium concentration of 0.05%, pH 4.5, in which the 3-1042 strain was cultured. Unlike the potassium source, almost no influence of magnesium addition was shown at 37° C., while on the contrary, at 40° C., the levels were higher when magnesium was added compared to when not added. In particular, the maximum value was recorded with a magnesium sulfate heptahydrate concentration of 0.15% (ethanol concentration 6.28%; productivity 1.05 g/l·h; yield 55.98%). Each value was higher compared to when not adding magnesium sulfate heptahydrate (ethanol concentration 6.08%; productivity 0.84 g/l·h; yield 54.22%). In regard to the magnesium sulfate concentration, there was a tendency that the ethanol concentration, the productivity, and the yield were all reduced when the addition was more or less than 0.15%, and it was shown that the optimum concentration was around 0.15%. Specifically, it has been revealed that it was effective to add an appropriate amount (preferably 0.15%) of magnesium source (magnesium sulfate) in the ethanol production using the yeasts provided by the present invention at 40° C. or higher.

In order to examine the influence of pH on ethanol production, 4 types of culture solutions which pH was adjusted from 4.0 to 5.5, from the syrup culture stock solution with a total sugar concentration of 22%, an ammonium sulfate concentration of 0.05%, and phosphoric acid-potassium concentration of 0.05%, in which the 3-1042 strain was cultured. At 37° C., the maximum levels were obtained for ethanol concentration (8.70%), productivity (1.45 g/l·h), and yield (77.5%) with pH 5.0. On the other hand, at 40° C., it was superior when with pH 5.5 compared to pH 5.0, where the maximum level in the 4 conditions were observed for ethanol concentration (6.78%), productivity (1.13 g/l·h), and yield (60.4%). The results of 0025 to 0029 are shown in the following Table 3.

TABLE 3

Influence of various nutrient sources on ethanol production at 37° C. and 40° C. for DMKU3-1942 strain

|  | At 37° C. | | | At 40° C. | | |
|---|---|---|---|---|---|---|
|  | Ethanol % (w/v) | Product.*¹ (g/l·h) | % of theoretical yield | Ethanol % (w/v) | Product. (g/l·h) | % of theoretical yield |
| Total sugars (%) | | | | | | |
| 16 | 6.26 (42)*² | 1.49 | 76.7 | 5.95 (48) | 1.42 | <u>72.6</u> |
| 18 | 6.92 (54) | 1.28 | 75.4 | 6.03 (48) | 1.26 | 65.7 |
| 20 | 7.77 (54) | 1.44 | <u>76.2</u> | 6.79 (48) | 1.42 | 66.5 |
| 22 | <u>8.29 (54)</u>*³ | <u>1.54</u> | 73.9 | <u>6.88 (54)</u> | 1.27 | 61.3 |
| 24 | 7.51 (60) | 1.25 | 61.4 | 6.54 (48) | <u>1.36</u> | 53.4 |
| (NH4)2SO4 (%) | | | | | | |
| 0 | 6.85 (72) | 0.95 | 61.0 | 6.22 (54) | 1.15 | 55.4 |
| 0.05 | 7.35 (54) | <u>1.36</u> | 65.5 | <u>6.60 (48)</u> | <u>1.37</u> | <u>58.8</u> |
| 0.07 | <u>7.80 (72)</u> | 1.08 | <u>69.5</u> | 6.27 (60) | 1.05 | 55.9 |
| 0.10 | 7.46 (72) | 1.04 | 66.5 | 6.41 (60) | 1.07 | 57.2 |
| KH2PO4 (%) | | | | | | |
| 0 | 6.92 (72) | 0.96 | 61.7 | <u>6.45 (60)</u> | 1.07 | <u>57.5</u> |
| 0.025 | 7.12 (72) | 0.99 | 63.5 | 6.02 (60) | 1.00 | 53.7 |
| 0.05 | <u>7.65 (72)</u> | <u>1.06</u> | <u>68.1</u> | 6.33 (72) | 0.88 | 56.4 |
| 0.10 | 7.55 (72) | 1.05 | 67.3 | 6.12 (54) | <u>1.13</u> | 54.6 |
| MgSO47H2O (%) | | | | | | |
| 0 | 7.31 (72) | 1.02 | 65.2 | 6.08 (72) | 0.84 | 54.22 |
| 0.05 | 7.25 (72) | 1.01 | 64.6 | 6.11 (54) | 1.13 | 54.50 |
| 0.10 | 7.24 (72) | 1.00 | 64.5 | 6.11 (60) | 1.02 | 54.43 |
| 0.15 | <u>7.39 (72)</u> | <u>1.03</u> | <u>65.9</u> | <u>6.28 (60)</u> | <u>1.05</u> | <u>55.98</u> |
| 0.20 | 7.12 (72) | 0.99 | 63.4 | 6.08 (60) | 1.01 | 54.22 |
| 0.30 | 6.94 (72) | 0.96 | 61.9 | 6.04 (72) | 0.84 | 53.87 |
| pH | | | | | | |
| pH 4.0 | 7.26 (96) | 0.76 | 64.7 | 5.94 (84) | 0.71 | 52.9 |
| pH 4.5 | 7.68 (96) | 0.80 | 68.5 | 5.78 (96) | 0.60 | 51.5 |
| pH 5.0 | <u>8.70 (60)</u> | <u>1.45</u> | <u>77.5</u> | 6.57 (60) | 1.09 | 58.5 |
| pH 5.5 | 8.50 (60) | 1.42 | 75.8 | <u>6.78 (60)</u> | <u>1.13</u> | <u>60.4</u> |

*¹productivity
*²number in parenthesis is the culture time
*³underlined numbers are the maximum level under the condition From the results of Table 3, the preferred composition of the medium for ethanol production using the 3-1042 strain of the present invention at a temperature condition of 37° C. and 40° C., respectively, is shown in the following Table 4.

TABLE 4

|  | Temperature condition | |
|---|---|---|
|  | 37° C. | 40° C. |
| Total sugars (possible range) | 22% (20-24%) | 22% (20-24%) |
| (NH4)2SO4 (possible range) | 0.07% (0.05-0.10%) | 0.05% (-0.10%) |
| KH2PO4 (possible range) | 0.05% (0.025-0.10%) | Not necessary (possible -0.10%) |
| MgSO4·7H2O (possible range) | Not necessary (possible -0.15%) | 0.15% (0.05-0.15%) |
| pH (possible range) | 5.0 (4.5-5.5) | 5.5 (5.0-5.5) |

According to Tables 3 and 4, a culture solution for a culture at 37° C. (total sugar concentration 22% by adding sucrose; ammonium sulfate concentration 0.05%; phosphoric acid-potassium concentration 0.05%; magnesium sulfate heptahydrate concentration 0.15%; pH 5.0); and a culture solution for a culture at 40° C. (total sugar concentration 22% by adding sucrose; ammonium sulfate concentration 0.05%; phosphoric acid-potassium concentration 0.05%; magnesium sulfate heptahydrate concentration 0.15%; pH 5.5) were prepared from a sugarcane juice culture stock solution as a culture solution for producing ethanol using the 3-1042 strain, and shaking culture (110 stroke/min) was conducted for each temperature condition. In FIG. 2, the change over time (horizontal axis; hours) for ethanol concentration (○=37° C., □=40° C., graph left vertical axis; % w/v) and yeast growth (●=37° C., ■=40° C., graph right vertical axis; shown by OD at 660 nm) in the culture step for each culture solution are shown. In a culture at 37° C., the ethanol concentration increased to the maximum of 8.7% 60 hours after. The productivity and yield herein, were 1.45 g/l·h and 77.5%, respectively. The absorbance (OD) at 660 nm reflecting the number of yeast cells, reached the first peak 24 hours later. The level slowly increased thereafter, and was 11.42 54 hours later, and 14.33 72 hours later. On the other hand in a culture at 40° C., the ethanol concentration almost came to equilibrium 42 hours later, and the maximum level was 67.8%. The productivity and yield herein, were 1.13 g/l·h and 60.4%, respectively. The absorbance at 660 nm almost came to equilibrium 18 hours later, while it slowly increased thereafter, and reached finally 13.55 72 hours later.

(Comparison of Ethanol-producing Ability with Yeast of the Genus *Saccharomyces*)

In order to standardize the ethanol-producing ability of DMKU 3-1042 strain, the ethanol-producing ability and cell growth at 30° C. and 45° C. were compared with those of KU1 strain, a standard strain of yeast *Saccaromyces cerevisiae* which is commonly used in ethanol production, under the same conditions. 3-1042 strain and KU1 strain were inoculated into YPD medium (1% yeast extract, peptone 2%, glucose 2%), a standard culture solution of yeast. Shaking culture (160 rpm) was conducted at 30° C. and 45° C., a sampling was conducted to the culture solution every 6 hours, and the OD660 value (index of growth) and ethanol concentration in the culture solution were measured. Measurement of ethanol concentration was conducted with a measurement method with an alcohol dehydrogenase which has been isolated and purified from an acetic acid bacterium (Gluconobacter suboxydans IFO12528) (Non-Patent Documents 4, 5). These results are shown in FIGS. 3 to 6.

FIGS. 3 and 4 show the growth curve of 3-1042 strain (▲) and KU1 strain (■) at 30° C. and 45° C., respectively. The vertical axis shows the OD660 value, and the horizontal axis shows the time course (hour) from the initiation of the culture. As it is clear from FIG. 3, the growth showed a similar transition for both strains at 30° C. On the other hand, at 45° C., almost no growth was observed for KU1 strain, while equal or faster growth as at 30° C. was shown for 3-1042 strain.

FIGS. 5 and 6 show the ethanol production of 3-1042 strain (Δ) and KU1 strain (□) at 45° C. and 45° C., respectively, in a graph. The vertical axis shows the ethanol concentration in a culture solution (% v/v; 1% corresponds to 0.8% in terms of w/v), and the vertical axis shows the time course from the initiation of the culture. As it is shown in FIG. 5, the ethanol-producing ability of 3-1042 strain at 30° C. showed a slight slow rising up to 6 hours, while attained the same level as KU1 strain 12 hours after. The transition thereafter was similar to that of KU1 strain. Specifically, concerning the basic characteristic of ethanol production, it has been shown that 3-1042 strain was comparable to a standard strain of *Saccharomyces cerevisiae*. At 45° C., while only a small amount (about 0.4%) of ethanol was contained in the culture solution for KU1 strain, reflecting the bad growth, equal or higher amount or ethanol (1% or more) as at 30° C. was contained for 3-1042 strain, from 6 hours and after. It was shown that the ethanol-producing ability of 3-1042 strain at that temperature is more than 2 times of that of a standard strain of *S. cerevisiae*, suggesting the effectiveness of 3-1042 strain under a high temperature condition.

EXAMPLE 3

(Examination of Ethanol-producing Ability—3 l Scale)

In order to investigate the ethanol-producing ability of DMKU 3-1042 strain at 37° C. in a 5 l-size culture vessel, 3 l of sugarcane juice culture solution (total sugar concentration 22% by adding sucrose; ammonium sulfate concentration 0.05%; phosphoric acid-potassium concentration 0.05%; magnesium sulfate heptahydrate concentration 0.15%; pH 5.0) was prepared. Further, in order to examine the effect of shaking and aeration in a large-scale culture, culture was performed with the following 4 conditions:

(1) shaking at 300 rpm (round per minute) only
(2) shaking at 300 rpm and aeration at 0.2 vvm (vessel volume per minute)
(3) shaking at 300 rpm, and aeration at 0.2 vvm for the first 12 hours
(4) shaking at 300 rpm and aeration at 0.2 vvm for the first 12 hours, and shaking at 150 rpm only thereafter The ethanol-producing ability for each of these conditions are compared and showed in the following Table 5. The lowest level was observed for the condition (1) of shaking only, where the ethanol concentration, productivity, and yield were the minimum in the 4 conditions. On the contrary, the highest levels were observed with the condition (2) of shaking and continuous aeration, where the ethanol concentration was 4.96%, productivity 1.3 g/l·h, and yield 57.1%. As for the OD660 value, index of cell density in a culture solution, it was lowest in (1) with 5.83, showing that, in a large scale culture system, no sufficient yeast growth was observed by only shaking, and that as a result, the ethanol concentration did not increase. This result was supported from the fact that the highest OD660 value (12.73) was observed in (2), where continuous aeration was performed, showing that to conduct an adequate aeration in addition to shaking is effective in ethanol fermentation using the thermotolerant ethanol-producing yeast provided by the present invention.

TABLE 5

Effect of shaking and aeration on culture at a 3 l scale

| | Ethanol concentration (%, w/v) | Ethanol productivity (g/l · h) | Yield (%) | Maximum level of OD660 (time recorded) |
|---|---|---|---|---|
| (1) shaking at 300 rpm only | 4.96 | 0.81 | 44 | 5.83 |
| (2) shaking at 300 rpm + aeration at 0.2 vvm | 6.43 | 1.3 | 57.1 | 12.73 (24 h) |
| (3) shaking at 300 rpm + aeration at 0.2 vvm (only for the first 12 hours) | 6.17 | Slightly larger than (1) | Slightly larger than (1) | 8.92 (36 h) |
| (4) shaking at 300 rpm + aeration at 0.2 vvm (for the first 12 hours) → shaking at 150 rpm only thereafter | 6.03 | Slightly larger than (1) | Slightly larger than (1) | 8.10 (44 h) |

EXAMPLE 4

(Comparison of Ethanol-producing Ability with a Standard Strain of *K. marxianus*)

The thermotolerant ethanol-producing yeast strain found in the present invention was compared with a standard strain of *K. marxianus*. As a standard strain, NRBC1777 strain (hereinafter referred to as 1777 strain, or as a standard strain) which has been provided from Incorporated Administrative Agency, National Institute of Technology and Evaluation (NITE), Biological Ressource Center (NBRC) was used. The same system used for the above comparison with yeast of the genus *Saccharomyces* was used, and specifically, 3-1042 strain, 3-118 strain, 3-p106 strain, 3-p1042 strain and NBRC 1777 strain were inoculated into YPD medium (1% yeast extract, 2% peptone, 2% glucose), a standard culture solution of yeast. Shaking culture (160 rpm) was conducted at 30° C. and 47° C., 48° C., and 49° C., a sampling was conducted to the culture solution every 6 hours, and the OD660 value (index of growth) and ethanol concentration in the culture solution were measured. Measurement of ethanol concentration was conducted with a measurement method with an alcohol dehydrogenase which has been isolated and purified from an acetic acid bacterium (Gluconobacter suboxydans IFO12528) (Non-Patent Documents 4, 5).

In FIG. 7, the growth curve of each strain of the present invention and the standard strain 1777 strain at 30° C. are shown. The vertical axis of the graph shows the OD660 value, and the horizontal axis shows the time course from the initiation of the culture. The growth of each strain of the present invention (3-1042=○, 3-p1042=●, 3-118=■, 3-p106=□) and of the 1777 strain (x) were visualized. Further, FIG. 8 shows the comparison of the ethanol-producing ability of each strain of the present invention and the 1777 strain at 30° C. Vertical axis shows the ethanol concentration (%, v/v), and horizontal axis shows the time (h) from the initiation of the culture. The 5 bar graphs (from the left side: 3-1042, 3-p1042, 3-118, 3-p106, NBRC 1777) show the ethanol production of each strain by time. As it is clear from FIGS. 7 and 8, it has been shown that there is no obvious difference for both growth and ethanol-producing ability between each stain provided by the present invention and the standard strain of *K. marxianus* at 30° C.

On the other hand, FIGS. 9 and 10 show the growth curve of each strain of the present invention and that of 1777 strain at 48° C. and 49° C. In both graphs, vertical axis shows the OD660 value, and horizontal axis shows the time (h) from the initiation of the culture. The symbols in the graph are the same as in FIG. 7 (3-1042=○, 3-p1042=●, 3-118=■, 3-p106=□, 1777 strain =x). As it is shown in both graphs, almost no growth is observed for the standard strain 1777 strain at 48° C., while a certain growth of approximately 9 by OD660 value was observed for each strain of the present invention. Further, at 49° C., no growth at all was observed for 1777 strain, while a growth of approximately 3 by OD660 value was observed for each strain of the present invention. It has been revealed that the thermotolerant ethanol-producing yeast provided by the present invention has an extremely superior thermotolerance compared with a standard strain of species *K. marxianus*.

Further, in FIGS. 11 and 12, the ethanol-producing ability of each strain of the present invention and that of 1777 strain at 48° C. and 49° C. are showed by comparison. In both graphs, vertical axis shows the ethanol concentration (%, v/v), and horizontal axis shows the time (h) from the initiation of the culture. The symbols in the graph are the same as in FIG. 8. As it is shown in both graphs, the ethanol-producing ability of each strain of the present invention are both superior at 48° C. and 49° C. compared to that of 1777 strain. Particularly, the ethanol-producing ability was shown to be more than 2 fold of the standard strain at 48° C.

(Influence of Sorbitol Addition)

In order to enhance the growth ability and ethanol-producing ability under a severe temperature condition of 48° C. and 49° C., the influence of sorbitol addition was investigated. The conditions of culture solution are the same as the above culture system, and specifically, sorbitol with a final concentration of 50 mM was added to YPD medium (1% yeast extract, 2% peptone, 2% glucose, 2% agar) to which 3-1042 strain, 3-118 strain, 3-p106 strain, 3-p1042 strain and NBRC 1777 strain were inoculated and cultured by shaking at 30° C., and 47° C., 48° C., and 49° C. A sampling was conducted to the culture solution every 6 hours, and the OD660 value (index of growth) and ethanol concentration in the culture solution were measured.

FIG. 13 shows the influence of sorbitol on growth under a culture condition of 48° C. In both graphs, the vertical axis shows the OD660 value, and the horizontal axis shows the time (h) from the initiation of the culture. "A" shows the results with sorbitol, and "B" the results without addition of sorbitol. The symbols in the graph are the same as in FIG. 7 (3-1042=○, 3-p1042=●, 3-118=■, 3-p106=□, 1777 strain=x). Compared to when sorbitol is not added, with a culture by adding sorbitol, all strains showed an increased growth ability shown by OD660, suggesting that the sorbitol addition was effective. FIG. 14 shows the results at 49° C., and "A" shows the results with sorbitol, and "B" the results without addition of sorbitol. The growth ability of the 4 strains of the present invention increased with the addition of sorbitol at 49° C., and a difference of 2 times or more was observed for OD660 value. However, this effect was not observed in the standard strain. It has been confirmed that the addition of sorbitol increases the growth ability of the thermotolerant ethanol-producing yeast strain of the present invention, at an extremely high temperature of 49° C. where no effect is observed in a standard strain.

FIGS. 15 and 16 show the effects of sorbitol on ethanol-producing ability under a culture condition of 48° C. and 49° C. In both graphs, vertical axis shows the ethanol concentration (%, v/v), and horizontal axis shows the time (h) from the initiation of the culture. "A" shows the results with sorbitol, and "B" the results without addition of sorbitol. The symbols in the graph are the same as in FIG. 8. At 48° C. shown in FIG. 15, the ethanol-producing ability of 1777 strain was increased, while it was only slightly increased for each strain of the present invention. On the contrary, under a condition of 49° C. shown in FIG. 16, the ethanol-producing ability was 3 times or more when sorbitol was added, compared to when not added. This level was not less that the level at 48° C. On the other hand, this effect was not observed for 1777 strain. In a sorbitol-added medium, ethanol concentration was dramatically increased 3 hours later from the initiation of the culture, and it was shown that the effect of sorbitol addition was exhibited in a culture of 3 hours or longer.

INDUSTRIAL APPLICABILITY

The thermotolerant ethanol-producing yeast provided by the present invention can be used in industry related to ethanol production, particularly ethanol production utilizing biomass. Particularly, the property of having an ethanol-producing ability even under a severe temperature condition of 40° C. or higher, leads to a cost down of ethanol production, and increase of fermentation efficiency.

The invention claimed is:

1. A method for producing ethanol comprising culturing a thermotolerant ethanol-producing yeast of species *Kluyveromyces marxianus* having an ethanol fermentation ability under a temperature condition of 40° C. or higher, wherein the culturing is conducted under a temperature condition of 40° C. or higher and in the presence of 10 to 100 mM of sugar alcohol.

2. The method for producing ethanol according to claim 1, wherein the sugar alcohol is sorbitol.

3. The method for producing ethanol according to claim 1, wherein the thermotolerant ethanol-producing yeast is cultured under a temperature condition of 40 to 49° C.

4. The method for producing ethanol according to claim 3, wherein the thermotolerant ethanol-producing yeast is represented by Deposit No: NITE BP-283, NITE BP-289, NITE BP-290, or NITE BP-291.

5. The method for producing ethanol according to any one of claims 1 to 4, wherein said culturing is in a culture solution comprising 15 to 25% sugar.

6. The method for producing ethanol according to any one of claims 1 to 4, wherein said culturing is in a culture solution comprising 15 to 25% of sugar as a main component, and at least one component selected from 0.01 to 0.5% ammonium salt, 0.01 to 0.5% potassium salt, and 0.01 to 0.5% magnesium salt as an auxiliary component.

7. The method for producing ethanol according to any one of claims 1 to 4, comprising culturing yeast under a temperature condition of 30 to 40° C., wherein said culturing is in a culture solution comprising 18 to 24% sugar as a main component, and 0.05 to 0.1% ammonium sulfate and 0.025 to 0.1% calcium phosphate as an auxiliary component, and which has a pH from 4.8 to 5.2.

8. The method for producing ethanol according to any one of claims 1 to 4, comprising culturing yeast under a temperature condition of 40° C. or higher, wherein said culturing is in a culture solution comprising 16 to 22% sugar as a main component, and 0.05 to 0.1% ammonium sulfate and 0.05 to 0.15% magnesium sulfate as an auxiliary component, and which has a pH from 5.3 to 5.7.

9. The method for producing ethanol according to any one of claims 1 to 4, comprising shaking at 150 to 450 rpm and aerating at 0.1 to 0.3 vvm.

10. The method for producing ethanol according to any one of claims 1 to 4, wherein a squeezed sugarcane juice is used as a raw material.

11. A thermotolerant ethanol-producing yeast represented by Deposit No: NITE BP-283.

12. A thermotolerant ethanol-producing yeast represented by Deposit No: NITE BP-289.

13. A thermotolerant ethanol-producing yeast represented by Deposit No: NITE BP-290.

14. A thermotolerant ethanol-producing yeast represented by Deposit No: N1TE BP-291.

15. A transformant obtained by modifying or introducing one or more genes in the thermotolerant ethanol-producing yeast according to any one of claims 11 to 14.

16. The method for producing ethanol according to claim 2, wherein the thermotolerant ethanol-producing yeast is cultured under a temperature of 40 to 49° C.

17. The method for producing ethanol according to claim 16, wherein the thermotolerant ethanol-producing yeast is represented by Deposit No: NITE BP-283, NITE BP-289, NITE BP-290, or NITE BP-291.

\* \* \* \* \*